United States Patent [19]

Harding, Jr.

[11] Patent Number: 5,027,075
[45] Date of Patent: Jun. 25, 1991

[54] APPARATUS FOR DETERMINATION OF PROBE CONTACT WITH A LIQUID SURFACE

[75] Inventor: John C. Harding, Jr., Framingham, Mass.

[73] Assignee: Nova Biomedical Corporation, Waltham, Mass.

[21] Appl. No.: 408,616

[22] Filed: Sep. 18, 1989

[51] Int. Cl.$^5$ .................... G01R 27/26; G05D 9/00
[52] U.S. Cl. .................. 324/662; 73/864.24; 340/620; 422/106
[58] Field of Search ............. 324/661, 662, 664, 676, 324/689, 71.1; 340/620; 73/864.24, 864.25, 304 C; 422/63, 67, 100, 106

[56] References Cited

U.S. PATENT DOCUMENTS

| | | | |
|---|---|---|---|
| 3,635,094 | 1/1972 | Oberli | 73/864.24 |
| 4,276,258 | 6/1981 | Ginsberg et al. | 422/64 |
| 4,326,851 | 4/1982 | Bello et al. | 73/864.24 |
| 4,389,900 | 6/1983 | Gutierrez | 73/861.42 |
| 4,615,351 | 10/1986 | Schliefer et al. | 137/2 |
| 4,716,536 | 12/1987 | Blanchard | 364/571 |
| 4,730,489 | 3/1988 | Hockstra | 73/304 |
| 4,736,638 | 4/1988 | Okawa et al. | 73/864.24 |
| 4,749,988 | 6/1988 | Berman et al. | 340/618 |

FOREIGN PATENT DOCUMENTS 1287148 8/1972 United Kingdom .

*Primary Examiner*—Kenneth Wieder
*Assistant Examiner*—Jack B. Harvey

[57] ABSTRACT

The occurrence of physical contact between a conductive probe and a surface of a liquid held in a container is detected as the probe is moved toward and eventually touches the liquid surface; a conductor is disposed on the other side of the container from the probe; an electrical signal is sent through the liquid between the conductive probe and the conductor, and the time when physical contact has occurred is determined based on when the resulting electrical signal which has passed through the liquid exceeds a threshold; and the threshold is determined based on the resulting electrical signal. In another aspect, the electrical signal is pulsed, and the resulting electrical signal is synchronously detected as the basis for determining when the physical contact has occurred. In another aspect, a non-conductive rotatable support holds the container and moves the container into position under the probe; a conductor is disposed beneath the rotatable support and in a fixed position relative to the rotatable support so that when the container is in position under the probe, the conductor lies beneath the container; the conductor has a limited extent so that when the container is not in that position no part of the conductor lies beneath the container.

23 Claims, 4 Drawing Sheets

APPARATUS FOR DETERMINATION OF PROBE CONTACT WITH A LIQUID SURFACE

BACKGROUND OF THE INVENTION

This invention relates to detecting the occurrence of physical contact between a conductive probe and a surface of a liquid held in a container, as the probe is lowered toward and eventually touches the liquid surface.

Such a probe may be used to remove a sample of a liquid, such as a biological specimen, from the container to perform testing. Typically, a number of sample containers, possibly representing different patients, are processed in sequence. Before the liquid can be retracted from a container, the system must ensure that the end of the probe is within the liquid volume since, if it is not, air, instead of the liquid sample, will be drawn into the probe.

Okawa et al., U.S. Pat. No. 4,736,638 ("Okawa"), detects when a pipette probe first touches a liquid in a container by capacitively coupling an AC signal via a conductive platter to the liquid in the container which rests above the platter. The magnitude of the resulting AC signal received by the probe as it is lowered into the container is measured as an indication of when the probe has touched the liquid surface. The signal magnitude is generally low until the probe contacts the liquid surface and then jumps to a higher level. Okawa's conductive platter is disk shaped to enable detecting when the probe contacts the liquid in any one of a number of containers arranged in a rack supported on the platter.

SUMMARY OF THE INVENTION

In one aspect, the invention features detecting the occurrence of physical contact between a conductive probe and a surface of a liquid held in a container, as the probe is moved toward and eventually touches the liquid surface; a conductor is disposed on the other side of the container from the probe; an electrical signal is sent through the liquid between the conductive probe and the conductor, and the time when physical contact has occurred is detected based on when the resulting electrical signal exceeds a threshold; the threshold is established based on the resulting electrical signal.

Preferred embodiments of the invention include the following features. The threshold is determined prior to the probe touching the liquid surface based on two values of the resulting electrical signal taken with the probe positioned at two distinct points above the surface. The threshold is set at a predetermined amount above the expected value that the resulting electrical signal would have if the probe were positioned at a predetermined point within the container.

In another aspect of the invention, the electrical signal sent through the liquid between the conductive probe and the conductor is pulsed, and the resulting electrical signal is detected synchronously as the basis for determining when the physical contact has occurred.

Preferred embodiments of the invention include the following features. A pulse generator supplies the electrical signal and a synchronous detector connected to the pulse generator detects the resulting electrical signal. The circuitry determines when the physical contact has occurred by detecting when a step change in the resulting electrical signal causes it to exceed the threshold.

In another aspect, the invention features a non-conductive rotatable support which holds the container and moves the container into position under the probe; a conductor is disposed beneath the rotatable support and in a fixed position relative to the rotatable support so that when the container is in position under the probe, the conductor lies beneath the container; and the conductor has a limited width so that when the container is not in that position no part of the conductor lies beneath the container.

In preferred embodiments, the conductor comprises an L-shaped plate that extends both below and to the side of the container, and the rotatable support comprises a tray which supports a plurality of containers, each of which may be positioned beneath the probe by rotation of the tray.

As a result, the non-conductive support can be economically manufactured by, e.g., injection molding. The synchronous detector and pulse generator provide a sensitive measurement of the resulting electrical signal. The L-shaped plate enhances the accuracy of the detection because the plate is adjacent the bottom of the container as well as the side of the container, therefore receiving more of the resulting signal. Calculating the threshold as the probe is moved toward the liquid surface, but before contact is made, results in greater accuracy in contact detection since the threshold is a function of the particular characteristics of the sample being analyzed (and mechanical tolerances). The threshold is set above the extrapolated value of the signal at the bottom of an empty cup (i.e., the maximum signal for an empty cup) to ensure that a reading above the threshold will indicate contact with the liquid. The tray holds a plurality of containers and is movable to allow many different samples to be positioned beneath the probe.

Other advantages and features will become apparent from the following description of the preferred embodiment and from the claims.

BRIEF DESCRIPTION OF THE DRAWINGS

We first briefly describe the drawings.

DETAILED DESCRIPTION OF THE PREFERRED EMBODIMENT

Figure 1:
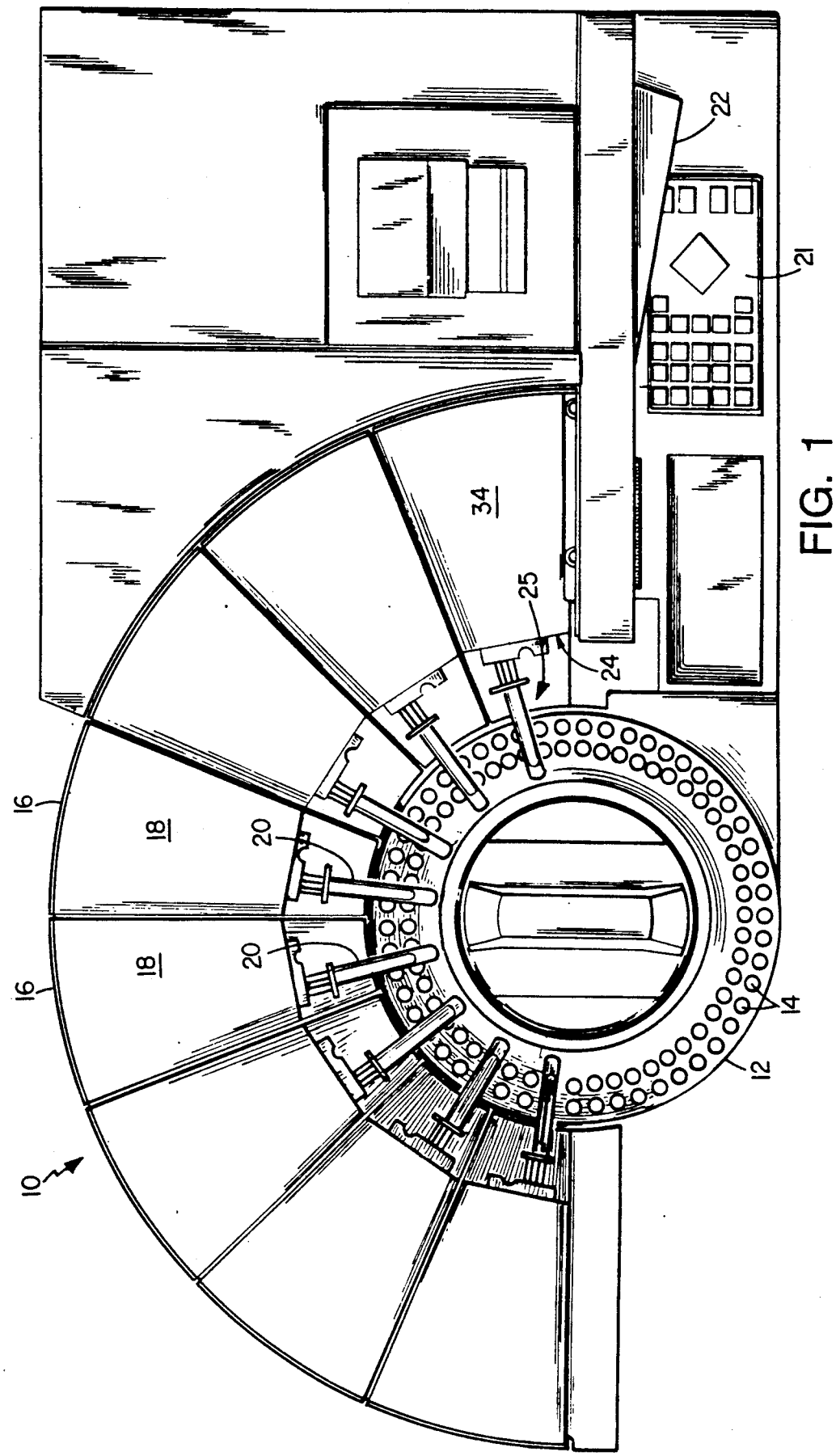
FIG. 1 is an top view of a biological liquid testing system.

Referring to FIG. 1, liquid testing system 10 includes a ring-shaped injection-molded nonconductive plastic tray 12 holding sample containers 14, 15, each of which contains a volume of a liquid to be tested. Tray 12 is rotatable to selectively position each sample container 14 adjacent a selected testing unit 16 among a number of testing units arranged around the tray. Each testing unit 16 includes a main compartment 18 and a carriage assembly 20.

Each carriage assembly 20 includes a probe 28 (FIG. 2) that can be lowered into a selected sample container when the container has been positioned beneath the probe by the rotation of tray 12. When lowered into the liquid, the probe can be used to withdraw a liquid sample and deliver it to the corresponding main compartment 18 for testing. Different testing units 16 may perform different tests on each sample as specified by a system operator. The operator directs the system via a keyboard 21 and a screen 22, and the testing is controlled by a computer (not shown).

A diluter unit 24, also located adjacent the tray, is arranged to dilute the sample for later testing. Diluter 24 has a main compartment 34.

Figure 2:
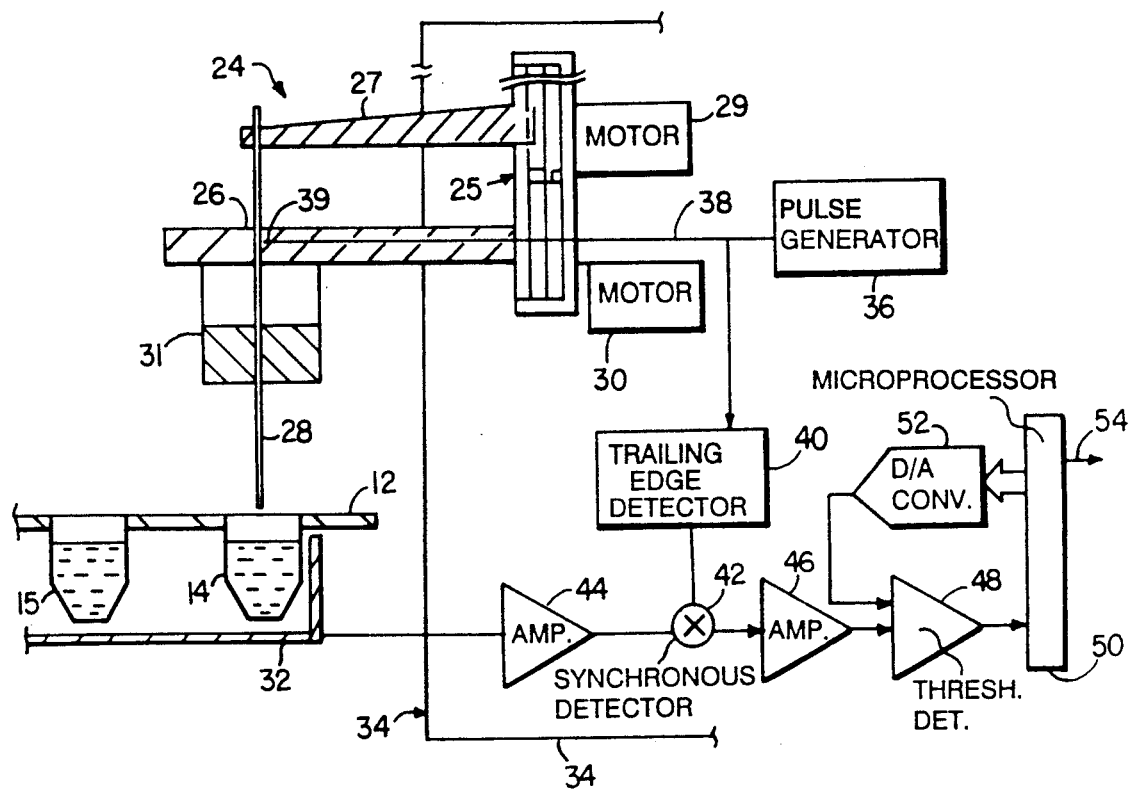
FIG. 2 is a cross-sectional schematic diagram of a portion of the liquid testing system and associated electronics.

Referring to FIG. 2, diluter unit 24 includes a carriage 25 having arms 26 and 27. Probe 28, a small diameter conductive (stainless steel) hollow cylinder, is held on carriage arm 27. A stepper motor 29 controls the vertical position of arm 27 using a gear arrangement (not shown) and thereby controls the vertical movement of probe 28. A second motor 30 controls the horizontal position of carriage 25 using another gear assembly (also not shown), thereby moving both arms 26 and 27 horizontally. Probe 28 passes through a septa assembly 31, attached to the underside of carriage arm 26. The septa assembly provides a mechanism for supplying liquids to the probe. A stationary L-shaped conductive plate 32 is mounted in a fixed position (indicated by arrow 25 in FIG. 1) relative to and beneath tray 12, and extends adjacent the tray and also beneath the two sample containers 14, 15 currently aligned with diluter unit 24. Plate 32 is generally only slightly wider than the diameter of the sample containers and does not extend beyond the portion of the tray located at position 25.

Main compartment 34 of diluter unit 24 includes a pulse generator 36 connected to probe 28 via a conductive wire 38 which passes through carriage arm 26 and contacts probe 28 at a sliding contact 39. A trailing edge detector 40 is connected between pulse generator 36 and a synchronous detector 42. Conductive plate 32 is connected to synchronous detector 42 through an amplifier 44. The circuit also includes an amplifier 46, a threshold detector 48, and a microprocessor 50. Microprocessor 50 is connected to threshold detector 48 through a D/A converter 52, and includes an output 54.

Operation

During testing, tray 12 is rotated to move the two sample containers 14, 15 into alignment with arms 26, 27 of carriage 25. Motor 30 adjusts the horizontal position of carriage 25 to align probe 28 with one of sample containers 14, 15, e.g., the one containing the sample to be diluted. The system does not know in advance how much liquid is in the container, and hence does not know the vertical position of the surface of the liquid.

Figure 3:
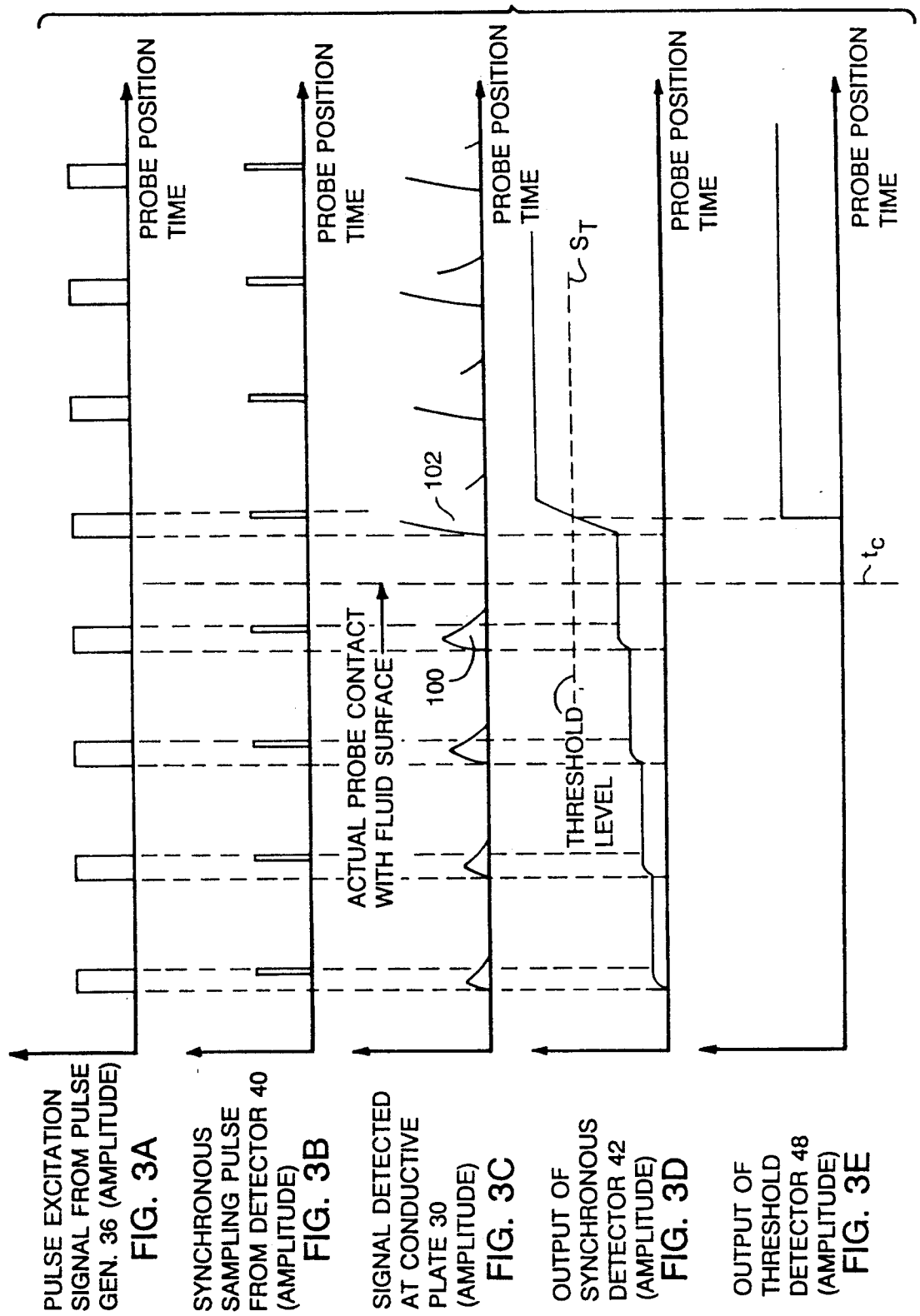
FIGS. 3A-3E are signal timing digrams.

Referring to FIG. 3, as probe 28 is lowered toward the liquid by stepper motor 29, a pulsed electrical potential (FIG. 3A) is applied to probe 28 by pulse generator 36. (Because the stepper motor lowers the probe at a steady rate, the signals shown in FIG. 3 are all functions of the probe position as well as time.) Before the probe touches the liquid, the signal of FIG. 3A passes through the air between the probe and the surface of the liquid, through the liquid sample itself, and through the space between the bottom of the liquid sample and plate 32, and is received by plate 32.

The signal received by plate 32 (FIG. 3C) is delivered to synchronous detector 42 through amplifier 44. The signal of FIG. 3C is shown amplified for clarity but the actual amplitude would be considerably less than the amplitude of the pulses of FIG. 3A. Synchronous detector 42 receives the sampling pulses illustrated in FIG. 3B from trailing edge detector 40 (as shown, the sampling pulses of FIG. 3B occur at the trailing edges of the pulses of FIG. 3A), and samples the signal received from plate 32 synchronously with the trailing edge detector sampling pulses, producing the signal of FIG. 3D.

As probe 28 approaches plate 32, the signal received by plate 32 (FIG. 3C) increases because the capacitance between probe 28 and plate 32 increases (capacitance between the probe and the plate is inversely proportional to the distance between them). Beginning with the next pulse following when the probe contacts the liquid (at time $t_c$), there will be a sharp increase in the amplitude of the signal received by the plate (note the change from signal pulse 100 to signal pulse 102) because the liquid effectively acts as a capacitive plate (the effect is similar to attaching a capacitive plate to probe 28). When the probe contacts the liquid "plate", the distance between the probe and plate 32 suddenly decreases since the liquid effectively shunts a portion of the distance between them. As discussed above, a decrease in the distance causes an increase in the capacitance. Furthermore, the surface area of the liquid is much greater than the surface area of the probe, and since the capacitance between two conductors is directly proportional to the surface areas of each conductor, this effective increase in surface area will also cause an increase in the total capacitance.

The output of synchronous detector 42 (FIG. 3D) is received by threshold detector 48. The step increase caused by probe contact with the liquid surface is evident in FIG. 3D and will at some time exceed a predetermined threshold $S_t$. Threshold detector 48 detects this increase beyond the threshold and delivers a signal to microprocessor 50 (FIG. 3E). The synchronous detector output (FIG. 3D) remains substantially constant once the probe has contacted the liquid because the the probe is effectively connected to the bottom of the liquid and the capacitance between the bottom of the liquid and the plate thus remains constant.

Threshold $S_t$ is determined as a function of the amount of liquid held in each sample container and the system determines a threshold for each container automatically and adaptively as the probe is lowered toward the container.

Figure 4:
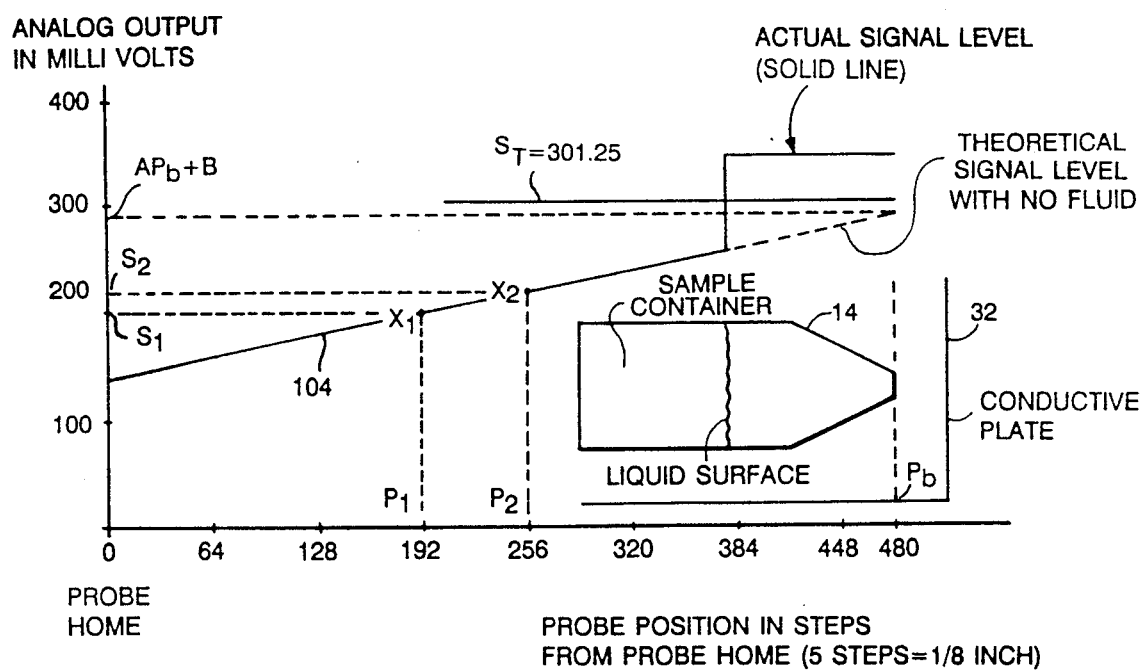
FIG. 4 is a graph that illustrates the relationship between the position of the probe and an electrical signal received by a plate positioned beneath a sample container.

Referring to FIG. 4, the output 104 of amplifier 46 as a function of probe position is indicated in millivolts, while the probe position (along the horizontal axis) is measured in "steps" corresponding to successive steps of stepper motor 29 that controls the probe's vertical position, five steps being approximately equal to one eighth of an inch (i.e., 0.125 inches). The steps are counted from "probe home" (count "0"), corresponding to the uppermost vertical position of the probe.

As the probe is lowered toward the liquid surface, two values of output voltage and probe position corresponding to two points above the top of the sample cup are supplied to microprocessor 50. This is accomplished by incrementing the value delivered to the DAC 52 (FIG. 2) and determining where the threshold detector 48 switches. The values are chosen at points above the top of the container to ensure that the probe has not yet contacted the surface of the liquid, for reasons explained below. Two illustrative such points $X_1$ and $X_2$ are shown in FIG. 4 but any points above the liquid surface could be chosen. Each point has a corresponding value of signal amplitude ($S_1$ and $S_2$, respectively)

and a corresponding probe position ($P_1$ and $P_2$, respectively). The positions of the sample container 14 and conductive plate 32 are also shown.

The threshold value ($S_T$) of signal amplitude used by threshold detector 48 is then calculated by microprocessor 50 as follows:

$$S_T = AP_b + B + \tfrac{1}{2}AC; \qquad \text{(Equ. 1)}$$

where A is the slope of curve 104 and is defined by $$A = \frac{S_2 - S_1}{P_2 - P_1}; \qquad \text{(Equ. 2)}$$

B is the projected signal level at step 0, defined by $$B = S_1 - AP_1; \qquad \text{(Equ. 3)}$$

C (empirically determined) is equal to 72.0 steps, and $P_b$ is equal to the probe position at cup bottom (step number 480).

In the example, point $X_1$ has an $S_1$ value of 200 millivolts and a $P_1$ value of 192 steps while point $X_2$ has $S_1$ and $P_1$ values of 220 millivolts and 256 steps, respectively. Thus, equation 2 yields an A value of 0.3125 millivolts/step. equation 3 yields a B value of 140 millivolts. The threshold value, $S_T$, is calculated using equation 1 and is equal to 301.25 millivolts. This value is provided to threshold detector 48 through D/A converter 52. Therefore, when threshold detector 48 detects a value greater than 301.25 millivolts, it will signal microprocessor 50 which will deliver a signal on output 54 indicating probe contact with the surface of the liquid.

Note that $AP_b + B$ is the projected signal value if the probe tip were at the bottom of an empty cup. The threshold is therefore set at a value equal to some number (i.e., $\tfrac{1}{2}AC$) above the extrapolated value of the signal amplitude at cup bottom. The value "C" is derived empirically and is approximately one half the expected step change that results when the liquid surface is contacted by the probe. This value of C can be used with most liquids since the step change is relatively independent of the type of liquid being analyzed.

Other embodiments of the invention are within the scope of the claims. For example, while in the preferred embodiment the pulse generator is coupled to the probe and the signal is received by plate 32, the signal could be coupled to the plate and received by the probe.

I claim:

1. Apparatus for detecting the occurrence of physical contact between a conductive probe and a surface of a liquid held in a container as the probe is moved toward and eventually touches the liquid surface, the apparatus comprising:
   a conductor disposed on the other side of said container from said probe,
   signaling circuitry for sending an electrical signal through said liquid between said conductive probe and said conductor, and for detecting when said physical contact has occurred based on when the resulting electrical signal which has passed through said liquid exceeds a threshold, and
   a threshold determiner for establishing said threshold based on said resulting electrical signal.

2. The apparatus of claim 1 wherein said threshold determiner is arranged to establish said threshold based on said resulting electrical signal prior to said probe touching said liquid surface.

3. The apparatus of claim 1 wherein said threshold determiner is connected to receive two values of said resulting electrical signal with said probe positioned at two distinct points above said surface and said threshold determiner is arranged to calculate said threshold value based on both said received values.

4. The apparatus of claim 1 wherein said threshold determiner is further arranged to calculate the expected value that said resulting electrical signal would have if the probe were positioned at a predetermined point within said container, and to set said threshold value to a predetermined amount above said expected value.

5. Apparatus for detecting the occurrence of physical contact between a conductive probe and a surface of a liquid held in a container as the probe is moved toward and eventually touches the liquid surface, the apparatus comprising:
   a conductor disposed on the other side of said container from said probe; and
   circuitry for sending a pulsed electrical signal through said liquid between said conductive probe and said conductor while said probe is being moved, and for synchronously detecting the resulting electrical signal as the basis for determining when said physical contact has occurred.

6. The apparatus of claim 5 wherein said circuitry comprises a pulse generator for supplying said electrical signal.

7. The apparatus of claim 6 wherein said circuitry comprises a synchronous detector for detecting said resulting electrical signal, and said pulse generator is connected to said synchronous detector.

8. The apparatus of claim 5 wherein said circuitry determines when said physical contact has occurred by detecting a step change in said resulting electrical signal.

9. The apparatus of claim 5 wherein said circuitry detects when said physical contact has occurred by detecting when said resulting electrical signal exceeds a threshold.

10. The apparatus of claim 9 further comprising a threshold determiner for receiving values of said resulting electrical signal and calculating said threshold based on said received values.

11. The apparatus of claim 10 wherein said threshold is determined based on the value of said resulting electrical signal with said probe positioned at two distinct points above said surface.

12. The apparatus of claim 10 wherein said threshold determiner is further arranged to calculate the expected value that said resulting electrical signal would have if the probe were positioned at a predetermined point within said container, and to set said threshold value to a predetermined amount above said expected value.

13. A method for detecting the occurrence of physical contact between a conductive probe and a surface of a liquid held in a container as the probe is moved toward and eventually touches the liquid surface, the method comprising:
   sending an electrical signal through said liquid between said conductive probe and a conductor disposed on the other side of said container from said probe while said probe is being moved,
   determining a threshold based on the resulting electrical signal which has passed through said liquid, and detecting when said physical contact has occurred based on when said resulting electrical signal exceeds said threshold.

14. The method of claim 13 wherein said step of determining comprises measuring the value of said resulting electrical signal with said probe positioned at two distinct points above said liquid surface.

15. The method of claim 14 wherein said step of determining comprises calculating the expected value that said resulting electrical signal would have if the probe were positioned at a predetermined point within said container, and setting said threshold value to a predetermined amount above said expected value.

16. The method of claim 15 wherein said expected value is calculated based on values of said resulting electrical signal with said probe positioned above said liquid surface.

17. A method for detecting the occurrence of physical contact between a conductive probe and a surface of a liquid held in a container as the probe is moved toward and eventually touches the liquid surface, the method comprising:
    sending a pulsed electrical signal through said liquid between said conductive probe and a conductor disposed on the other side of said container from said probe, and
    synchronously detecting the resulting electrical signal as the basis for determining when said physical contact has occurred.

18. The method of claim 17 wherein said step of synchronously detecting comprises detecting a step change in said resulting electrical signal.

19. The method of claim 17 wherein said step of synchronously detecting comprises detecting when said resulting electrical signal exceeds a threshold.

20. Apparatus for detecting the occurrence of physical contact between a conductive probe and a surface of a liquid held in a container as the probe is moved toward and eventually touches the liquid surface, the apparatus comprising:
    a non-conductive rotatable support for holding said container and moving said container into position under said probe,
    a conductor disposed beneath said rotatable support and in a fixed position relative to said rotatable support so that when said container is in said position said conductor lies beneath said container and on the other side thereof from said probe, said conductor having a limited extend so that when said container is not in said position no part of said conductor lies beneath said container, and
    circuitry for sending a pulsed electrical signal through said liquid between said conductive probe and said conductor while said probe is being moved, and for synchronously detecting the resulting electrical signal as the basis for determining when said physical contact has occurred.

21. The apparatus of claim 20 wherein said conductor comprises a plate.

22. The apparatus of claim 21 wherein said plate is L-shaped and extends both beneath and adjacent said rotatable support.

23. The apparatus of claim 20 wherein said rotatable support comprises a tray which supports a plurality of containers, each of which may be positioned beneath said probe by rotation of said tray.

* * * * *